United States Patent
Presswood, Jr. et al.

(10) Patent No.: US 9,216,905 B2
(45) Date of Patent: Dec. 22, 2015

(54) GASIFICATION OR LIQUEFACTION OF COAL USING A METAL REACTANT ALLOY COMPOSITION

(76) Inventors: Ronald G. Presswood, Jr., Houston, TX (US); Ian C. Bishop, Houston, TX (US)

(*) Notice: Subject to any disclaimer, the term of this patent is extended or adjusted under 35 U.S.C. 154(b) by 125 days.

(21) Appl. No.: 13/487,430

(22) Filed: Jun. 4, 2012

(65) Prior Publication Data

US 2012/0304822 A1    Dec. 6, 2012

Related U.S. Application Data

(60) Provisional application No. 61/493,247, filed on Jun. 3, 2011.

(51) Int. Cl.
*F27D 3/16* (2006.01)
*C10J 3/57* (2006.01)
*C01B 17/033* (2006.01)
*C01B 31/02* (2006.01)

(52) U.S. Cl.
CPC .............. *C01B 17/033* (2013.01); *C01B 31/02* (2013.01); *C10J 3/57* (2013.01); *F27D 3/16* (2013.01); *C10J 2300/093* (2013.01); *C10J 2300/0969* (2013.01); *C10J 2300/1675* (2013.01)

(58) Field of Classification Search
CPC .............. F27D 3/16; F27D 10/08; C10J 3/57
USPC .................. 266/216, 241, 157, 155, 265, 236; 110/216, 104 R; 48/92
See application file for complete search history.

(56) References Cited

U.S. PATENT DOCUMENTS

| | | | | |
|---|---|---|---|---|
| 4,649,867 A | * | 3/1987 | Cordier et al. | 122/5 |
| 6,264,722 B1 | * | 7/2001 | Kepplinger et al. | 75/445 |
| 6,322,745 B1 | * | 11/2001 | Leigh et al. | 266/44 |
| 7,335,320 B2 | * | 2/2008 | Kindig et al. | 252/373 |
| 2006/0208400 A1 | * | 9/2006 | Schmeler | 266/280 |
| 2007/0183966 A1 | * | 8/2007 | Nakagawa et al. | 423/648.1 |
| 2010/0283009 A1 | * | 11/2010 | Nickels et al. | 252/373 |

FOREIGN PATENT DOCUMENTS

CN         201273767 Y    * 7/2009

OTHER PUBLICATIONS

Derwent Acc-No. 2009-L89064 for patent family CN 201273767 Y by Li et al published Jul. 15, 2009. Abstract.*

(Continued)

*Primary Examiner* — George Wyszomierski
*Assistant Examiner* — Tima M McGuthry Banks
(74) *Attorney, Agent, or Firm* — Morgan, Lewis & Bockius LLP

(57) ABSTRACT

This invention relates to a method and apparatus for gasifying or liquifying coal. In particular, the method comprises reacting a coal with a molten aluminum or aluminum alloy bath. The apparatus includes a reaction vessel for carrying out the reaction, as well as other equipment necessary for capturing and removing the reaction products. Further, the process can be used to cogenerate electricity using the excess heat generated by the process.

10 Claims, 3 Drawing Sheets

(56) References Cited

OTHER PUBLICATIONS

Machine translation for CN 201273767 Y published Jul. 15, 2009 (downloaded from Google Patents).*

Helmensteine, Todd. "Use the Activity Series of Metal to Predict Reactivity." About.com Chemistry. About.com, Dec. 22, 2010. Web. Jun. 11, 2014. <http://chemistry.about.com/od/chartstables/a/Activity-Series-Of-Metals.htm>.*

* cited by examiner

GASIFICATION OR LIQUEFACTION OF COAL USING A METAL REACTANT ALLOY COMPOSITION

This application claims priority to U.S. Provisional Patent Application 61/493,247 filed Jun. 3, 2011.

FIELD OF THE INVENTION

The present invention relates to a method to gasify or liquefy coal and to capture and recover carbon, sulfur, hydrocarbons, and heavy metals from the coal using a molten aluminum or alloy bath composed of aluminum or an aluminum alloy that includes, but is not limited to zinc, iron, copper, silicon and calcium alloys.

BACKGROUND OF THE INVENTION

Although a number of methods exist to gasify or liquefy coal, these methods are costly and in some cases create a secondary waste that can be more of a problem than the actual gas stream itself. Currently, coal gasification or liquefacation methods create greenhouse gases such as carbon monoxide carbon dioxide, as well as, other bi-products such as tar, ammonia, and tar-water emulsions. Further, these processes also produce slag, which currently must be land filled and there is currently no efficient method to recovery heavy metals, such as mercury, that typically are found in coal. While these processes work, they require significant energy input or create waste streams that must be disposed of at a cost to the operator and with potential future environmental impact. Thus, there is a need in the art for an improved method to economically gasify or liquefy coal while recovering the remaining carbon, sulfur and any heavy metals.

SUMMARY OF THE INVENTION

The present invention provides an apparatus for gasifying or liquefying coal. The coal can be any coal from peat (a coal precursor) to lignite (60% carbon) to anthracite (90+% carbon). The process utilizes a molten aluminum or molten aluminum alloy bath. The aluminum can be alloyed with metals that include, but are not limited to zinc, iron, copper, silicon, and calcium. The coal is ground and can be dried, and then the powder is introduced into the bath below the surface. The powdered coal is forced below the surface using an inert gas such as Nitrogen or argon. In the process excess heat is generated and can be used to facilitate other processes such as cogeneration of power. As the coal is passed through the bath, the aluminum or aluminum alloy bath reacts with the coal to break it down to its elemental parts. These elements are then removed from the bath using a gravimetric process and a gas capture process. The elements removed from the bath can include, but are not limited to, carbon, sulfur, hydrogen, nitrogen, mercury, copper, iron, as well as other heavy metals. The process can also produce methane and other hydrocarbons. The elemental materials can be recovered and sold and the hydrocarbons are recovered and sold or burned to facilitate the process. The inert gas is reprocessed and reused.

The aluminum or aluminum alloy bath is able to remove oxygen compounds by chemically reacting with them at high temperature. This allows the carbon bonds of the coal to be broken, producing volatile organic compounds, as well as elemental compounds.

This process has been evaluated in laboratory tests using ground lignite coal. The ground coal was passed through molten aluminum. The flue gas produced and the final alloy mass were analyzed using scanning electron microscope. (See Table 1).

TABLE 1

Process Mass Analysis

|  | MOL % |
|---|---|
| H2 | 25.181 |
| CO2 | 27.345 |
| CO | 14.265 |
| C | 19.898 |
| C2 | 2.824 |
| C2 | 2.999 |
| C3 | 0.939 |
| C3 | 2.228 |
| C4 | 0.199 |
| C4 | 1.034 |
| C4 | 0.000 |
| C5 | 0.199 |
| C6 and above | 2.888 |
|  | 100 |

FIG. 1 shows the basic process flow. In the basic process, powdered coal is introduced below the surface of the molten metal bath 103 using an injection feed system 101 through feed line 102. The elemental material, such as carbon, sulfur and the like, is captured 104, less dense secondary compounds are removed from the surface of bath 105, and denser secondary compounds are removed from the bottom of the bath 106. While this has been described as a method to gasify or liquefy coal, use of this method to other organic compounds, such as, for example, peat, wood, and grass are also contemplated.

BRIEF DESCRIPTION OF THE DRAWINGS

For a more complete understanding of the present invention, reference is now made to the following descriptions taken in conjunction with the accompanying Figures and drawings, in which.

DETAILED DESCRIPTION OF THE INVENTION

The present invention provides a process to gasify or liquefy coal. The process utilizes a molten aluminum or molten aluminum alloy bath. The process utilizes a molten aluminum bath as the reactant. The coal, which is introduced below the surface of the molten aluminum bath, reacts with the aluminum to decompose the coal. In the process, elemental carbon, sulfur, copper, iron, and heavy metals and molecular hydrogen, nitrogen, methane, and other hydrocarbons are removed from the molten bath. The products can be sold and the nitrogen is either vented to the atmosphere or captured.

The process utilizes a molten metal as the primary reactant. In the preferred embodiments the molten metal is aluminum or an aluminum bath. The aluminum can also be alloyed with other elements including, but not limited to, zinc, iron, copper, silicon, magnesium, and calcium. Other metals and metal alloys such as calcium and silicon are also envisioned. The flue gas stream, which contains oxygen containing greenhouse gases produced by combustion processes, is passed through the aluminum alloy bath to remove the oxygen-containing gases from the flue gas stream.

In the process, excess heat is generated and can be used to facilitate other processes such as cogeneration of power. The excess generated by the process is a function of the makeup of the greenhouse gases in the flue gas feed.

When the coal contains other compounds, those compounds can also be decomposed or captured. For example, if the coal contains inorganic compounds, such as chlorine, the process will produce an aluminum salt, in this case aluminum chloride. The present invention also provides a method and apparatus for capturing heavy metals, such as, but not limited to mercury, which is often found in coal. In the process, the molten metal bath breaks down the metal compounds as they are introduced into the molten metal bath. As additional aluminum is added to the bath, the heavy metals settle to the bottom of the reaction vessels and are removed from the reaction vessel. While some aluminum may be entrained in the heavy metals that are removed from the bottom of the reaction vessel, the aluminum can be removed and refined and the heavy metals can be captured.

Figure 1:
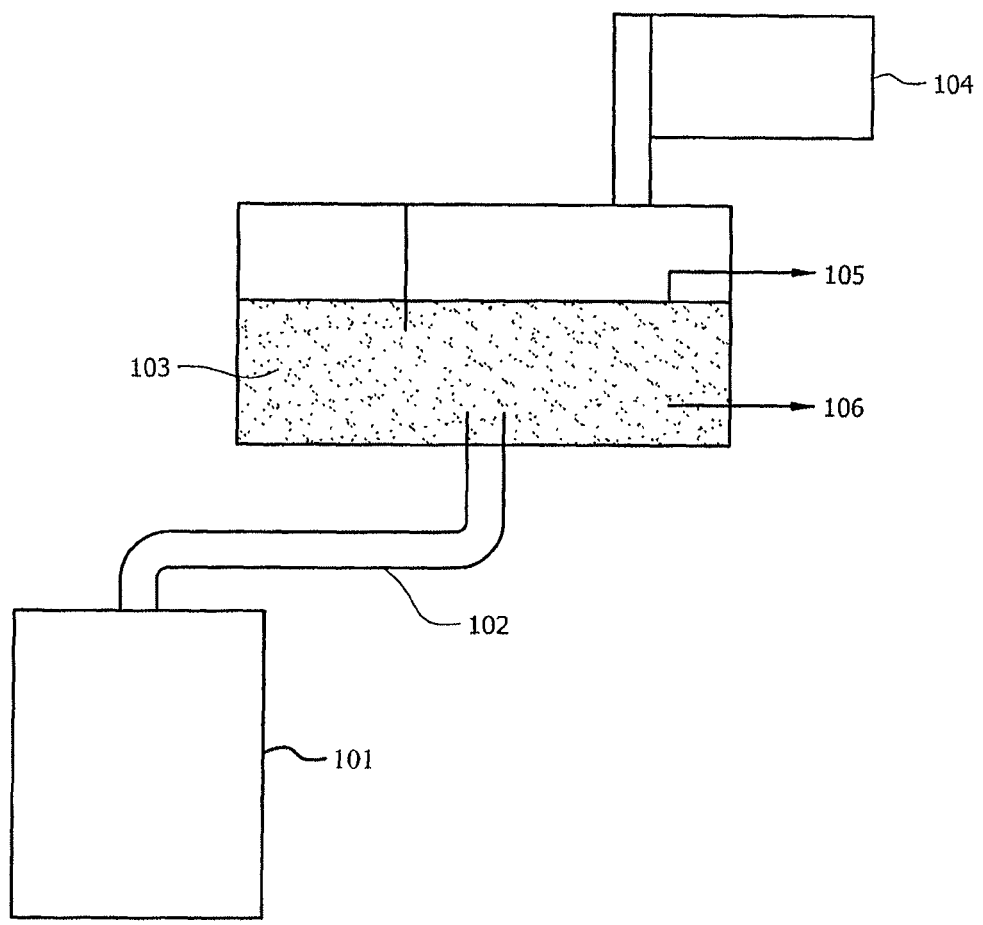
FIG. 1 shows the basic process flow.
Figure 2:
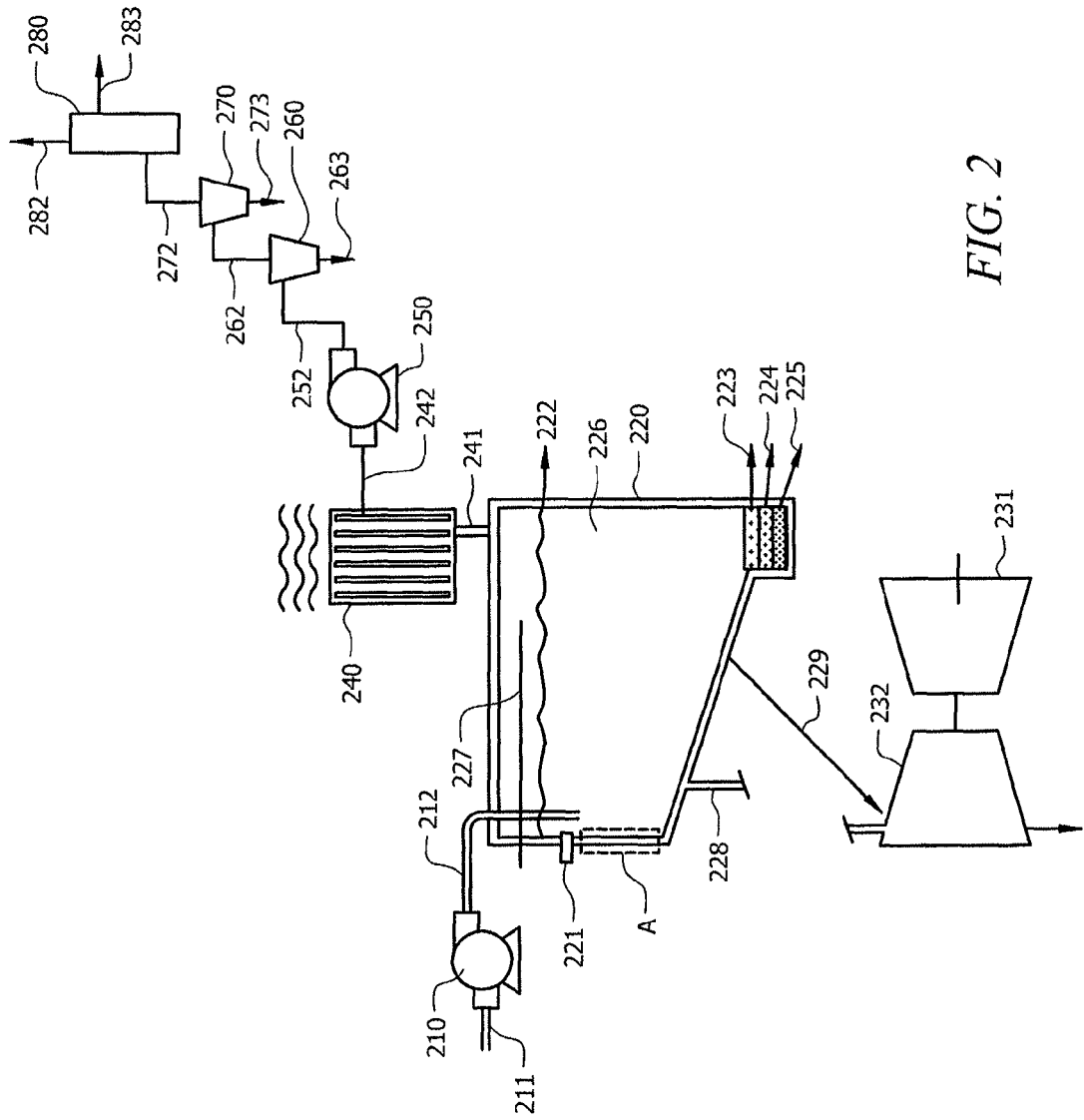
FIG. 2 shows a typical process flow.

A detailed process flow is shown in FIG. 2. While the process described discusses processing coal, other organic materials can be processed using the invention. The ground coal is introduced into the treatment process through blower feed line 211. Blower 210 is used to inject the ground coal into reaction vessel 220 through injection line 212. Injection line 212 introduces the ground coal stream, which is entrained in an inert gas such as nitrogen, below the surface 222 of the molten aluminum compound 226. Injection line 212 must be sufficiently below the surface 222 of the molten aluminum compound 226 to allow for sufficient mixing. The heavy products of the reaction, typically the heavy metals described above will settle out in the reaction vessel. The reaction vessel typically has a sloped bottom, however other designs such conical and the like can be utilized. Once the heavy products settle out, they are collected using collection lines 223, 224, and 225. Collection lines 223, 224, and 225 allow for heavy metals of different densities to be removed. Depending on the size of the process, the heavy products can be continuously removed or a batch removal process can be used.

Reaction vessel 220 also includes an aluminum feed line 221, which is used to supply additional aluminum compound to replace that consumed by the reaction with the ground coal. Additional heat may be required during start-up, for example. Heater 227 is provided for this purpose. Heater 227 can be any type heater, including radiative, inductive, and convective. For example, heater 227 would be a microwave heater or a radio frequency heater wherein the frequency is tuned for the metal alloy used.

Figure 3:
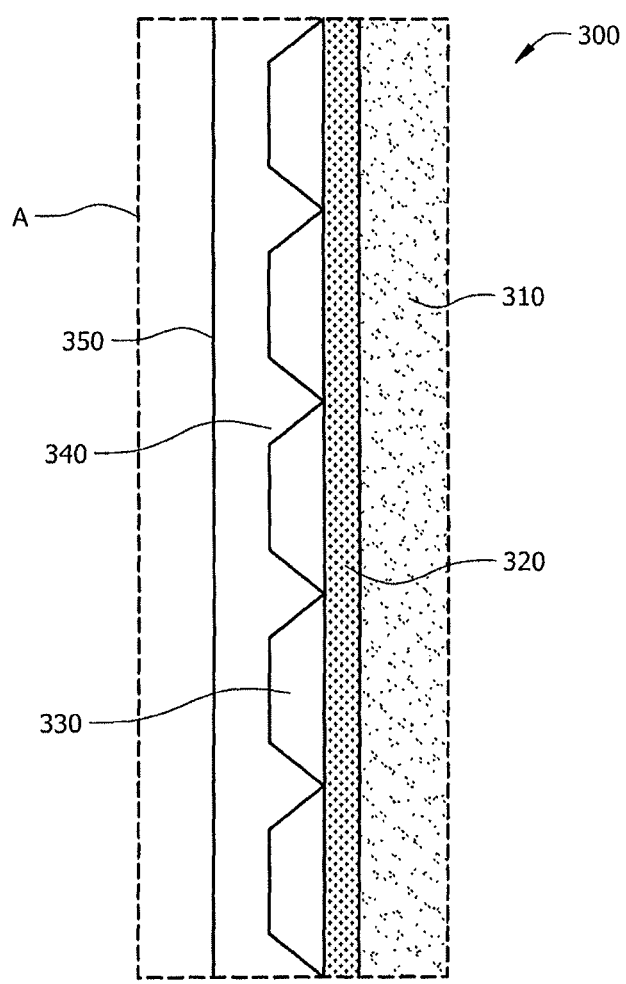
FIG. 3. shows a detailed cross sectional view of the reaction vessel wall.

Thus, the heat generated by the process must be removed. Section A, which is shown in more detail in FIG. 3 shows one way the heat can be removed from the process. The reaction vessel 220 is lined with a refractory material 310, which protects the vessel wall 320. Cooling plate 330 is attached to the vessel wall 320 and cooling water is circulated in the channels created between the cooling plant 330 and the vessel wall 320. Insulation 340 surrounds the cooling plate to maximize heat recovery, as well as for safety purposes. Once the cooling water picks up the heat generated from the process, it can be either sent to a cooling tower or the heat can be recovered and used for other purposes. If the process is used in a facility that needs a hot water source, then the heat recovery system can be designed for this purpose. However, the heat can also be used to generate electricity.

Turning back to FIG. 2, a steam turbine electric generation process is represented. In this case, the cooling water is introduced thorough cooling feed 228. As the cooling water travels around the reaction vessel 220, it picks up heat and steam is generated. The steam generated is then sent via steam line 229 to steam turbine 232. The steam passes through the turbine and as it condenses, turns the turbine blades of turbine 232. Turbine 232 is coupled to generator 231. As the turbine turns the rotor of generator 231 though the stator, it generates electricity. While this process is only briefly described, this steam turbine-electric generator process is well known in the art. And any steam turbine-electric generator process could be utilized.

Also, as described above, the reaction will also produce elemental carbon, elemental sulfur, molecular nitrogen and molecular hydrogen. These will be removed from the reaction vessel using blower 250. Blower 250 will pull high temperature elemental carbon, elemental sulfur, molecular nitrogen and molecular hydrogen from the reaction vessel 220 through heat exchanger feed line 241 into heat exchanger 240. Heat exchanger 240 will then cool this material to enable further processing. Any hydrocarbons that are produced may also be condensed in heat exchanger 240. These liquid hydrocarbons can be collected for further use or sale. Heat exchanger 240 can be any heat exchanger, however in the preferred embodiment, heat exchanger 240 is a forced air heat exchanger, however other heat exchangers, are also envisioned. The process steam then leaves the heat exchanger through line 242 and passes through blower 250 and blower discharge line 252 into two cyclone separators. The first separator 260 separates out carbon from process stream. The carbon is collected though separation line 263. The remaining process stream proceeds through line 262 to the second separator 270, which separates out sulfur from the process stream. The sulfur is collected through separation line 273. The remaining process stream, which may include gaseous nitrogen and hydrogen, is then sent through line 272 and separated in cryo unit 280. In this unit, the gas stream is cooled further and to allow the components to be separated into different components that are sent through lines 282 and 283.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An apparatus for producing gasified and liquefied products from solid coal particles, the apparatus comprising;
   a reaction vessel designed to hold a molten metal and form an upper surface of molten metal,
   an injection line projecting into the molten metal through the upper surface for introducing a stream of coal into the vessel at a sufficient distance below the upper surface of the molten metal for mixing the coal into the molten metal, an injector blower to force the stream of coal through the injection line and into the molten metal, an inlet in the reaction vessel for replacing molten metal consumed by reaction in the reaction vessel, the reaction vessel being shaped with a bottom so that liquefied products heavier than the molten metal will settle to the bottom, at least one lower outlet for removing said liquefied products from the reaction vessel, the reaction vessel further comprising an upper outlet above the upper surface of the molten metal for receiving reaction gas from the molten metal, a heat exchanger connected to the upper outlet downstream from the reaction vessel for producing gasified and/or liquefied products from the reaction gas, a removal mechanism blower for removing the reaction gas through the upper outlet of the reaction vessel and transporting it to the heat exchanger, and at least one separator for removing particulate matter from the gasified and/or liquefied products.

2. The apparatus of claim 1, wherein the reaction vessel further comprises a reaction vessel wall, a refractory material, and a cooling plate, wherein the cooling plate forms a channel for a cooling fluid between the cooling plate and the reaction vessel wall.

3. The apparatus of claim 1 further comprising a steam turbine.

4. The apparatus of claim 1 further comprising an electric generator.

5. The apparatus of claim 1, wherein the molten metal is aluminum.

6. The apparatus of claim 1, wherein the molten metal is aluminum alloy.

7. The apparatus of claim 6, wherein the molten aluminum alloy includes at least one alloy material selected from the group consisting of silicon, magnesium, zinc, copper, iron, and calcium.

8. The apparatus of claim 1, wherein the molten metal is silicon.

9. The apparatus of claim 1, wherein the molten metal is alloy.

10. The apparatus of claim 1, wherein the inlet in the reaction vessel for replacing molten metal consumed by reaction in the reaction vessel comprises a feed line extending through the wall of the reaction vessel.

\* \* \* \* \*